(12) United States Patent
Pauly et al.

(10) Patent No.: US 6,511,684 B1
(45) Date of Patent: Jan. 28, 2003

(54) USE OF PLANT EXTRACTS WITH AN ANTI-RADICAL-TYPE ACTION

(75) Inventors: Gilles Pauly, Nancy (FR); Christian Moretti, Paris (FR)

(73) Assignee: Cognis France (Societe Anonyme), Saint Martory (FR)

( * ) Notice: Subject to any disclaimer, the term of this patent is extended or adjusted under 35 U.S.C. 154(b) by 0 days.

(21) Appl. No.: 09/857,445

(22) PCT Filed: Nov. 30, 1999

(86) PCT No.: PCT/EP99/09294

§ 371 (c)(1),
(2), (4) Date: Jun. 4, 2001

(87) PCT Pub. No.: WO00/32162

PCT Pub. Date: Jun. 8, 2000

(30) Foreign Application Priority Data

Dec. 3, 1998 (FR) .............................................. 98 15380

(51) Int. Cl.⁷ ................................................ A61K 35/78
(52) U.S. Cl. ...................... 424/773; 424/725; 424/401; 424/78.02; 424/78.03; 424/757; 424/451
(58) Field of Search ................................. 424/725, 757, 424/773, 400, 401, 451, 78.02

(56) References Cited

U.S. PATENT DOCUMENTS 5,756,109 A * 5/1998 Burger et al.

FOREIGN PATENT DOCUMENTS

JP           10139680 A    *   5/1998
JP           20-139680         5/1998

OTHER PUBLICATIONS

Franca et al., "Plants used in the treatment of leishmanial ulcers due to Leishmania (Viannia) braziliensis in an endemic area of Bahia Brazil", Rev Soc Bras Med Trop, 1996, May/Jun.; 29 (3): 229–32.*

P. Delaveau et al., Stimulation of the Phagocytic Activity of Reticuloendothelial System by Plant Drugs, Fac. Sci. Pharm. Biol., vol. 40, No, 1, Karlsruhe, De, Fichier Chemical Abstracts vol. 93:1979959 XP–002115094.

A. Caceres et al, Plants Used in Guatemala for the Treatment of Respiratory Diseases: . . ., *Journal of Ethnopharmacology,* (1993) 1993:417511 XP–002115095.

A Caceres et al., Plants Used in Guatemala for the Treatment of Dermatophytic Infections . . . , *Journal of Ethnopharmacology,* (1991) vol. 31, No. 3, Karlsruhe, DE, Fichier Biosis, 1991:24700 XP–002115096.

* cited by examiner

Primary Examiner—Leon B. Lankford, Jr.
Assistant Examiner—Ruth A. Davis
(74) Attorney, Agent, or Firm—Young & Thompson

(57) ABSTRACT

The use of plant extracts, especially plant extracts with an anti-radical-type action, and a cosmetic or dermopharmaceutical composition containing extracts of this type. The use of at least one plant extract whose botanical genus belongs to the group formed by the following: Clidemia, Inga, Sabicea, Astrocaryum, Siparuna, Eperua, Byrsonima, Priva, Coutoubea and Goupia genera; as an active substance which has especially anti-radical-type activities, for preparing a cosmetic or dermopharmaceutical product for local, external use for the skin, the mucous membranes and/or the epithel or appendage structures.

6 Claims, No Drawings

USE OF PLANT EXTRACTS WITH AN ANTI-RADICAL-TYPE ACTION

The invention relates to the cosmetics field, particularly to the use of plant extracts in dermo-cosmetics, and its object is the use of certain medicinal herbs from French Guyana for the preparation of cosmetic or dermo-pharmaceutical products for the skin, mucous membrane and/or the epithelium or body appendages (hair, nails etc).

The Creole and Palikur peoples of French Guyana use numerous local plants in their traditional medicine. These plants and their therapeutic use are described particularly in the work entitled: "Pharmacopées traditionelles en Guyane: Créoles. Palikur, Wayapi" by Grenand P., Moretti C. and Jacquemin H., published by Orstom in 1987.

The authors of this invention have however discovered that extracts of certain plants of the above-mentioned type have various biological and biochemical actions linked with very high cutaneous tolerance, which enables them to be used directly in compositions for cosmetic use and particularly in dermo-cosmetics.

The plants chosen by the inventors therefore enable extracts to be obtained, all of which unexpectedly and surprisingly have a stronger anti-radical-type action but also an inhibiting action on tyrosinase (de-pigmenting), on tyrosinase activators (pigmenting), an anti-UVA and anti-UVB action, an action protecting catalase from UVA, and an anti-elastase, anti-collagenase, anti-gylcation and/or lypolytic action (for slimming).

The main object of the invention is therefore to use at least one extract of a plant of a botanical genus belonging to the group formed by Clidemia, Inga, Sabicea, Astrocaryum, Siparuna, Eperua, Byrsonima, Priva, Coutoubea or Goupia as an active ingredient, particularly with an anti-radical action, in the preparation of a cosmetic or dermo-pharmaceutical product for external, topical use on the skin, mucous membrane and/or epithelium or body appendages.

The following particular species may advantageously be selected from the above-mentioned genera:

*Clidemia hirta, Clidemia dentata*

*Inga bourgoni, Inga pezizifera, Inga alata, Inga alba, Inga capitata, Inga meissneriana*

*Sabicea cinerea, Sabicea glabrescens, Sabicera velutina, Sabicea villosa, Sabicea hirsuta*

*Eperua falcata*

*Byrsonima verbascifolia, Byrsonima crassifolia, Byrsonima chrysophylla, Byrsonima coriacea*

*Astrocaryum vulgare, Astrocaryum murumuru, Astrocaryum chambira, Astrocaryum jauari, Astrocaryum macrocalyx*

*Priva lappulacea*

*Coutoubea spicata, Coutoubea ramosa*

*Siparuna guianensis, Siparuna emarginata*

*Goupia glabra*

In a preferred embodiment of the invention however, giving extracts with a qualitatively and quantitatively optimised action particularly in respect of the anti-radical-type action, the active ingredient comprises at least one extract of a plant selected from the group formed by *Clidemia hirta, Inga bourgoni, Sabicea cinerea, Astrocaryum vulgare, Siparuna guianensis, Eperua falcata, Byrsonima verbascifolia, Priva lappulacea, Coutoubea spicata* and *Goupia glabra*.

Owing to their many forms of action these extracts are advantageously used alone or combined together or with other active compounds in products designed mainly to control ageing skin, hyper-pigmentation of the skin, patches of pigment, loss of skin elasticity, wrinkles, irritation and inflammation (treatment of sensitive skin types), irritation caused by environmental pollution and/or sunshine and/or for slimming formulae.

The parts of the plants used to prepare and obtain the above-mentioned extracts are chosen from roots, cortices (roots, stalks and/or trunk of plants), leaves and foliated stalks, fruit, grains and/or blossoms.

When the parts of the appropriate plants have been gathered and dried they are subjected to an extraction process. The solvent used may advantageously be selected from the group formed by water, alcohols, ketones, esters, types of ether, chlorine-containing solvents or polyhydric alcohols, or mixtures of at least two of the above-mentioned miscible solvents.

In a special embodiment of the present invention the extract or extracts is/are obtained by an extraction process based on wave radiation, for example microwaves or ultrasound.

The extracts involved in the invention may alternatively be obtained by extraction of supercritical $CO_2$, alone or mixed with a secondary solvent.

In a special embodiment of the present invention the plant extract(s) comprise(s) one or more separated fractions, purified particularly by chromatography and based on one or more extracts of said plants obtained by one of the aforementioned extraction processes.

To illustrate the invention, though without restricting its scope, various processes which can be carried out to prepare the above-mentioned plant extracts will now be described.

In the following examples the parts of the plants used are only given as an indication. The extracts involved in the invention can be obtained from any accessible parts of the aforementioned plants.

EXAMPLE 1

Cortices of Epurea falcata trunk are crushed then mashed finely by a blade-type pulping machine.

Three liters of distilled water are put into a reactor with an agitator then the following operations are successively carried out, comprising:

adding 300 g of pulped cortex to the reactor extracting with agitation for an hour while boiling cooling to ambient temperature removing the insoluble materials by centrifuging or filtering filtering the materials floating on the surface to a porosity of about 0.45 $\mu$m collecting the filtrate extracting the residue with 2 liters of distilled water under the same operating conditions and proceeding as described above after determining the content of dry material relative to the aqueous extracts obtained, adding substance of the malto dextrin type to obtain ⅔ added substance to ⅓ extracted dry material de-watering the solution obtained, by spraying or another method known to a person skilled in the art (dehydrating, freeze drying—lyophilisation, drying in a drying chamber etc).

The total yield of dry extract from this process is 15% by weight relative to the cortices.

EXAMPLE 2

Cortices of Inga bourgoni trunk are crushed then mashed finely by a blade-type pulping machine.

Three liters of 50% ethyl alcohol (ethanol) are put into a reactor with an agitator then the following operations are successively carried out, comprising:

- adding 300 g of pulped cortex to the reactor
- extracting with agitation for an hour and with (reflux) heating
- cooling to ambient temperature
- removing the insoluble materials by filtering
- filtering the materials floating on the surface to a porosity of about 0.45 μm
- collecting the filtrate
- extracting the residue with 1.5 liter of 50% ethanol under the same operating conditions then proceeding as described above
- evaporating the alcohol phase of both filtrates under vacuum
- after centrifuging and determining the content of dry material, if necessary making the addition to the aqueous phases obtained in the same proportions as mentioned in Example 1
- if necessary de-watering (dehydrating) the solution obtained, by conventional methods.

The total yield of dry extract from this process is 13.8% by weight relative to the cortices.

EXAMPLE 3

Cortices of the roots of Byrsonima verbascifolia are crushed then mashed finely by a blade-type pulping machine.

Three liters of 80% methyl alcohol (methanol) are put into a reactor with an agitator then the following operations are successively carried out, comprising:

- adding 300 g of pulped cortex to the reactor
- extracting with agitation for an hour and with (reflux) heating
- cooling to ambient temperature
- filtering off the insoluble materials
- filtering the materials floating on the surface to a porosity of about 0.45 μm
- collecting the filtrate
- extracting the residue with 1.5 liter of 80% methanol under the same operating conditions then proceeding as described above
- evaporating the methanol phase of both filtrates under vacuum
- after centrifuging and determining the content of dry material, making the addition to the aqueous phase obtained in the same proportions as described in Example 1
- if necessary de-watering the solution by conventional methods.

The total yield of extract obtained by this method is 17.4% by weight relative to the cortices.

EXAMPLE 4

Roots of Astrocaryum vulgare are crushed then finely pulped.

Three liters of absolute ethanol are put into a reactor with an agitator then the following operations are successively carried out, comprising:

- adding 300 g of crushed Astrocaryum vulgare roots to the reactor
- extracting with agitation for an hour and with (reflux) heating
- cooling to ambient temperature
- filtering off the insoluble materials
- filtering the materials floating on the surface to a porosity of about 0.45 μm
- collecting the filtrate corresponding to Extract 1
- extracting the residue with 3 liters of ethanol under the same operating conditions then proceeding as described above to obtain Extract 2
- evaporating the ethane phase of both filtrates under vacuum at 40° C.
- removing the traces of solvent by drying the extracts in a ventilated drying oven at 40–50° C.

7.15 g E1 extract and 1.47 g E2 extract are thus obtained and are finally mixed, representing a total yield of extract of 2.87% by weight relative to the roots.

The following table contains a list of all the plants and extracts with which the inventors worked, as an indication.

| Plant | Plant parts extracted | Type of extract | % yield (2 successive extractions) | Appearance |
|---|---|---|---|---|
| Clidemia hirta | Leaves | Aqueous extract | 20.9 | Brown powder |
| Inga bourgoni | Cortices | Aqueous extract | 9.7 | Wine-red powder |
| | | Ethanol E 50% | 13.8 | Wine-red powder |
| | | Ethanol extract | 11.7 | Wine-red powder |
| Sabicea cinerea | Foliated stalks | Aqueous extract | 16.4 | Brown powder |
| | | Ethanol E 50% | 25.5 | Brown powder |
| | | Ethanol extract | 18.7 | Green paste |
| Astrocaryum vulgare | Roots | Aqueous extract | 5.3 | Brown powder |
| | | Ethanol E 50% | 5.6 | Brown powder |
| | | Ethanol extract | 2.8 | Brown-orange paste |
| Siparuna guianensis | Leaves | Aqueous extract | 16.1 | Brown powder |
| | | Methanol E 80% | 21.9 | Brown powder |
| | | Ethanol extract | 22.6 | Green paste |
| Eperua falcata | Cortices | Aqueous extract | 15 | Brown powder |
| | | Methanol E 80% | 17.6 | Brown powder |
| | | Ethanol extract | 16.7 | Brown paste |

-continued

| Plant | Plant parts extracted | Type of extract | % yield (2 successive extractions) | Appearance |
|---|---|---|---|---|
| *Byrsonima verbascifolia* | Root cortices | Aqueous extract | 10.8 | Brown powder |
| | | Methanol E.80% | 17.4 | Brown powder |
| | | Ethanol extract | 15.7 | Brown paste |
| *Priva lappulacea* | Foliated stalks | Aqueous extract | 24.0 | Brown powder |
| | | Methanol E 80% | 14.5 | Brown powder |
| | | Ethanol extract | 13.9 | Brown paste |
| *Goupia glabra* | Leaves | Aqueous extract | 30.0 | Brown-orange powder |
| | | Methanol E 80% | 30.4 | Yellowish powder |
| *Coutoubea spicata* | Stalks + ears | Aqueous extract | 18.5 | Brown powder |
| | | Methanol E 80% | 18.8 | Brown powder |
| | | Ethanol extract | 18.0 | Brown-green paste |

It was possible for the biological and biochemical properties and actions of the plant extracts studied, which may be used directly in products of cosmetic importance, to be determined and measured by tests known to a person skilled in the art. The principles of the tests will be briefly discussed below and the results will be set out in the corresponding tables.

1) Anti-radical-type Action

The oxidative anti-stress properties were evaluated by "in tubo" and "in vitro" tests.

The group of in tubo tests includes both the initial radical-type forms of oxygen and the reactive forms introduced in vivo: radical hydroxyl (HO° and anion superoxide ($O_{\overline{2}}$).

1) "Chemical" Tests in Tubo a) Anti-DPPH Test

DPPH (diphenylpicryl hydrazyl) is a free, stable, violet-coloured radical which, in its leuco derivative, is modified by substances which capture free radicals (neutralising effect, also described as a "scavenger effect").

The result is given as percent inhibition of DPPH° in radical form relative to the control material without extract.

b) Anti-HO° Test with Salicylic Acid (Fenton Reaction)

The HO° (formed by $H_2O_2$ with $Fe^{++}$ and EDTA present) hydroxylate the salicylic acid, which then forms a reddish compound.

The optical density at 490 nm corresponds to the hydroxylated salicylic acid content.

An anti-radical substance reacts with the HO° radicals and reduces the formation of this red compound.

The results are given as percent inhibition of the hydroxylation content (average of 2 tests).

c) Anti-HO° Test with Deoxyribose (Fenton Reaction)

The HO° (formed by $H_2O_2$ with $Fe^{++}$ and EDTA present) oxidise the deoxyribose to aldehyde derivatives which are then metered by thiobarbiturate acid.

The thiobarbiturate acid is condensed with the aldehydes to form a pink compound (DO at 532 nm).

The Fenton reaction is also carried out without EDTA in order to measure the ability to complex iron; the deoxyribose is then oxidised by HO°.

The results are given as percent inhibition (an average of 2 tests).

2) "Biochemical" in Tubo Tests=Anti-anion Superoxide $O_{\overline{2}}$ Tests

An anti-radical substance absorbs either $H_2O_2$ or $O_{\overline{2}}$ or $O_2^1$, thereby reducing the formation of luminescence.

c) Anti-$O_{\overline{2}}$ Action: Method with NBT (Tetrazole Salt)

An enzyme system (hypoxanthine/xanthine oxidase) forms superoxide anions $O_{\overline{2}}$ which react with the NBT to form a red composition, formazan.

An anti-radical substance absorbs or destroys $O_{\overline{2}}$, thereby reducing the formation of formazan.

The results of these three tests a), b) and c) are given as percent inhibition (average of 2 tests).

The results of above-mentioned tests 1) and 2) are set out in the following table:

| | | ARL (%1) | Fenton test (%1) | | HX + XOD test (%1) | | |
|---|---|---|---|---|---|---|---|
| Plant | Type of extract | DPPH | Salicylic acid | Deoxy-ribose | Lum | Lum + M | NTB |
| *Clidemia hirta* | Aqueous extract | 91 | 40 | 70 | 99 | 51 | 53 |
| *Inga bourgoni* | Aqueous extract | 94 | | 40 | 100 | 98 | 64 |
| | Ethanol E 50% | 94 | | 27 | 100 | 98 | 71 |
| | Ethanol extract | 95 | | 74 | 100 | 99 | 83 |
| *Sabicea cinerea* | Aqueous extract | 90 | 47 | 39 | 99 | 89 | 41 |
| | Ethanol E 50% | 94 | 39 | 50 | 100 | 99 | 62 |
| | Ethanol extract | 93 | 51 | | 100 | 98 | 50 |
| *Astrocaryum vulgare* | Aqueous extract | 76 | | | 98 | 27 | 23 |
| | Ethanol E 50% | 93 | | | 100 | 98 | 74 |
| | Ethanol extract | 93 | 48 | 59 | 100 | 100 | 81 |
| *Siparuna guianensis* | Aqueous extract | 92 | | | 99 | 67 | 47 |
| | Methanol E 80% | 94 | | 47 | 100 | 99 | 71 |
| | Ethanol extract | 38 | 49 | | 99 | 96 | 54 |

Xanthine oxidase is an enzyme which is introduced during oxidative stress and catabolises the purine bases (adenine and guanine) to uric acid and $O_2^-$.

$O_2^-$ is dismutated spontaneously (or by SOD=superoxide dismutase) to $H_2O_2$ and $O_2$.

a) Anti-$O_2^-$ Action: Method with Luminol $O_2^-$ can be recognised in terms of luminescence by Luminol.

An enzyme system (hypoxanthine/xanthine oxidase) forms the superoxide anions $O_2^-$ which react with Luminol to form an intermediate compound. When stabilised this compound emits luminescence which is picked up by a photomultiplier.

A substance with an anti-radical action absorbs or destroys the anion $O_2^-$ thereby reducing the formation of luminescence.

b) Anti-$O_2^-$ and $H_2O_2$ Action: Method with Luminol in the Presence of Microperoxidase An enzyme system (hypoxanthine/xanthine oxidase) forms the superoxide anions $O_2^-$ which are gradually dismutated to $O_2^-$ and $H_2O_2$.

$H_2O_2$ and $O_2^-$ react with the microperoxidase (M) to form $O_2^1$ (singlet oxygen) which degrades Luminol (Lum), forming a luminescent compound, the light emission from which is picked up by a photomultiplier.

| | | | | | | | |
|---|---|---|---|---|---|---|---|
| Eperua | Aqueous extract | 91 | | 100 | 85 | 49 | |
| falcata | Methanol E 80% | 91 | | 99 | 94 | 61 | |
| | Ethanol extract | 94 | 64 | 100 | 100 | 89 | |
| Byrsonima | Aqueous extract | 95 | 80 | 100 | 100 | 83 | |
| verbascifolia | Methanol E 80% | 95 | 84 | 100 | 100 | 75 | |
| | Ethanol extract | 94 | 75 | 100 | 100 | 80 | |
| Priva | Aqueous extract | 95 | 46 | | 100 | 70 | 35 |
| lappulacea | Methanol E 80% | 100 | 51 | 45 | 100 | 97 | 45 |
| | Ethanol extract | 93 | 37 | | 100 | 96 | 44 |
| Goupia glabra | Aqueous extract | 96 | 49 | 32 | 100 | 94 | 34 |
| | Methanol E 80% | 89 | 61 | 31 | 100 | 90 | |
| Coutoubea | Aqueous extract | 92 | 79 | | 99 | 41 | |
| spicata | Methanol E 80% | 93 | 81 | | 100 | 89 | |
| | Ethanol extract | 92 | 72 | | 99 | 50 | |

Lum: Luminol; Lum+M: Luminol+microperoxidase

II) Anti-UVA Cell Protection On Human Fibroblasts in "in vitro" Survival

A) Metering of the salted-out MDA (Morliere P. and colleagues: "UV-A induced lipid peroxydation in cultured human fibroblasts", Biochim. Biophys. Acta 1084, 3: 261–269,1991).

1) The Theory

The UV-A penetrate into the dermis, where they set up an oxidative stress indicated particularly by lipoperoxidation of the cytoplasmic membranes.

Lipoperoxides are fragmented into malonal dialdehyde, which will crosslink/connect many biological molecules, for example proteins (enzyme inhibition) and nuclein bases (mutagenesis).

2) The Procedure

The fibroblasts are injected into a culture medium defined by calf's foetus serum.

The plant extract (in the culture medium defined by 2% serum) is added 72 hours after injection.

After 48 hours' incubation at 37° C. and $CO_2$=5% the culture medium is replaced by a saline solution and the fibroblasts are irradiated with a dose of UV-A (15 J/cm$^2$).

When irradiation is over the MDA (malonal dialdehyde) rate in the saline solution floating on the surface is metered and the protein rate in the fibroblasts is measured.

MDA is metered by the reaction on thiobarbiturate acid, and proteins by the so-called Bradford method.

B) Protecting the Action of the Catalase Enzyme from UVA

1) The Theory

UVA penetrates into the dermis where it sets up an oxidative stress, causing a lessening of the action of many enzymes including catalase.

Catalase is an enzyme which enables the $H_2O_2$ produced spontaneously by oxidation of substrates such as glucose or hypoxanthine to be removed.

$H_2O_2$ has to be removed quickly, otherwise it forms very toxic hydroxyl radicals (HO°) if iron is present.

2) The Procedure (by L H Johansson and L A H Borg in "A spectrophotometric method for determination of catalase activity in small tissue samples", Anal. Biochem. 174, 331–336, 1988).

Fibroblasts are injected into a culture medium defined by calf's foetus serum.

The plant extract (dissolved in a defined culture medium containing 2% serum at a concentration of 0.01 to 0.05% by wt/vol) is added 72 hours after injection.

After 48 hours' incubation at 37° C. and $CO_2$=5% the culture medium is replaced by a saline solution and the fibroblasts are irradiated with a dose of UV-A (5 J/cm$^2$)

When irradiation is over the rate of the active catalase is metered by a spectrophotometric method and its activity is related to the protein rate measured in the fibroblasts.

The action of the plant extract is given as a percent increase in catalase activity relative to the irradiated control material in the absence of any plant extract (two tests on average).

III) Evidence of the Anti-UVB Cell Protection Effect on Human Keratin Cells in "in vitro" Survival 1) The Theory UV-B causes slight inflammation (erythema, oedema) by activating an enzyme, phospholipase A2.

This enzyme removes the arachidonic acid from the phospholipids of the plasmic membrane. Arachidonic acid is the precursor of prostaglandins, including E2 prostaglandins (=PGE2), which are formed by cyclooxygenase.

2) The Procedure

A431 keratin cells are injected into a culture medium defined by calf's foetus serum. After 72 hours' incubation at 37° C. and $CO_2$=5% the culture medium is replaced by a saline solution containing the plant extract to be tested. The keratin cells are immediately irradiated with a dose of UV-B (30 mJ/cm$^2$) and incubated for 24 hours at 37° C., then the PGE2 and LDH rates in the culture medium floating on the surface are measured.

The number of adhering keratin cells is determined by a particle counter (after trypsination) and the PGE2 rate by an ELISA test.

The LDH (lactate dehydrogenase) rate is also determined by an enzyme reaction. LDH is a cytoplasmic enzyme which marks cell disorders.

The activity of the plant extract is tested and given as the percent inhibition of the two markers relative to the values reached with the control materials (2 tests on average, each in duplicate).

IV) "Anti-protease" Activity

The proteases which have been separated from the neutrophil polymorphonuclear substance during a slight inflammation or by fibroblasts exposed to UV-A radiation cause decomposition of the proteins which structure the extracellular matrix of the dermis.

Two types of protease were tested by enzyme reactions in tubo.

1) Anti-elastase test (Bieth J., "Elastase: structure, function and pathological role", Front Matrix Biol. 6: 1–82, Karger, 1978).

PNN segregate an elastase which is active on elastins (serine protease), proteoglycans and collagens.

The in tubo tests are carried out on an elastase from the pancreas (serine protease) using two types of substrate: a synthetic, chromogenic one (SS test) and a natural substrate, namely elastin combined with Congo red (Rc test).

The incubations take 30 minutes at ambient temperature or 2 hours at 37° C. and the colouring effects are in each case measured at 410 and 520 nm.

The inhibition proof mass which is tested as a comparison is α-1 antitrypsin.

2) Anti-collagenase in tubo test (Van Wart and colleagues, "A continuous spectrophotometric assay for Clostridium histolyticum collagenase", Anal. Biochem., 113, 356–365, 1981).

Collagenase is segregated by PNN during a slight inflammation and by the "old" or irradiated fibroblasts.

The tests are carried out with a clostridium hystoliticum collagenase and a synthetic chromogenic substrate, FAL-GPA.

Incubation takes 30 minutes at ambient temperature and the optical density is measured at 324 nm.

The results are given as percent inhibition of the enzyme relative to the control material without activator.

The inhibition control material tested as a comparison is cysteine.

The results of test series II) III) and IV) are listed in the following table:

MDA: malonal dialdehyde, PGE2: prostaglandin E2, LDH: lactate dehydrogenase, %1: percent inhibition relative to control material.

V) Inhibition of Melanogenesis

1) Inhibition of Tyrosinase "in Tubo"

Tyrosinase is the key enzyme in the synthesis of the melanin in the melanocytes of the human skin.

This enzyme catalyses the first two stages in the conversion of tyrosine to melanin, i.e. oxidation of melanin to DOPA (dihydroxyphenylalanine) and subsequently to dopachrome.

Dopachrome is a coloured compound which is quantified at 475 nm by spectrophotometry.

The activity of the enzyme used in tubo (obtained from fungi) is determined as 20 seconds by the kinetics of the reaction.

The proof mass substance is hydroquinone (C150= 0.025% wt/vol).

The results are expressed as percent inhibition relative to the control material.

2) Inhibition of Melanogenesis On B16 Melanocytes in the "in vitro" Culture

Inhibition of melanogenesis is assessed by spectrophotometric dosing of the melanin produced by melanocytes (B16 line), incubated "in vitro" in the presence of the plant extract to be tested.

The B16 melanocytes are cultivated in a defined growth medium and incubated for 3 days at 37° C., $CO_2$=5%. The

| Plant | Type of extract | UV-A (%1) MDA | Catalase % increase in activity/ radiated control material | UV-B (%1) PGE2 | LDH | Elastase (%1) Rc | SS | Collagenase (%1) |
|---|---|---|---|---|---|---|---|---|
| Clidemia hirta | Aqueous extract | 23 | | | 67 | 92 | 67 | 93 |
| Inga bourgoni | Aqueous extract | 71 | | 78 | 92 | 72 | 34 | 100 |
| | Ethanol E 50% | 70 | | 58 | 85 | 91 | 38 | 100 |
| | Ethanol extract | | | | 100 | 100 | 51 | |
| Sabicea cinerea | Aqueous extract | 74 | | 95 | 100 | | 68 | 83 |
| | Ethanol E 50% | 86 | | 40 | 75 | | 60 | 100 |
| | Ethanol extract | 78 | 81 | 87 | 100 | | 47 | 27 |
| Astrocaryum vulgare | Aqueous extract | 91 | | 78 | 97 | | 9 | 15 |
| | Ethanol E 50% | 82 | | 68 | 79 | 29 | 56 | 100 |
| | Ethanol extract | 75 | | 79 | 83 | 100 | 75 | 91 |
| Siparuna guianensis | Aqueous extract | 79 | | 60 | 86 | | 29 | 36 |
| | Methanol E 80% | 72 | 55 | 50 | 75 | 78 | 62 | 99 |
| | Ethanol extract | | | | | | | 21 |
| Eperua falcata | Aqueous extract | 79 | | 100 | 100 | | | 36 |
| | Methanol E 80% | 66 | | 99 | 100 | | | 85 |
| | Ethanol extract | 59 | | 88 | 93 | | 49 | 72 |
| Byrsonima verbascifolia | Aqueous extract | 63 | 23 | 70 | 92 | 100 | 68 | 100 |
| | Methanol E 80% | 66 | 26 | 64 | 89 | 101 | 86 | 100 |
| | Ethanol extract | 42 | 24 | 50 | 73 | 100 | 68 | 100 |
| Priva lappulacea | Aqueous extract | 26 | | 21 | 27 | | | |
| | Methanol E 80% | | | | | | | |
| | Ethanol extract | | | | | | 70 | 99 |
| Goupia glabra | Aqueous extract | | | | | | | |
| | Methanol E 80% | | | | | | | |
| Coutoubea spicata | Aqueous extract | | | | | | | |
| | Methanol E 80% | | | | | | | |
| | Ethanol extract | | | | | | | 47 | plant extracts are dissolved in a medium which activates melanogenesis and put into contact with the B16 for 3 days at 37° C.

The rate of salted-out melanin in the medium floating on the surface is quantified by spectrophotometry at 475 nm.

The rate of intra-cellular melanin is quantified by spectrophotometry at 475 nm in the homogenised B16 cells, which have been dissolved in a mixture of NaOH 1N+10% (v/v) DMSO.

The protein rate in the homogenised B16 cells is quantified by the so-called Bradford method.

The comparative substances are hydroquinone and arbutin.

VI. Evidence of Activity Inhibiting Non-enzymatic in Tubo Glycation ("Anti-glycation Activity")

(DEYL and colleagues: "Increased glycation and pigmentation of collagen in aged and young parabiotic rats and mice", Mechanisms of ageing and development, 55, 39–47, 1990/MONNIER and colleagues: "Accelerated age-related browning of human collagen in diabetes mellitus", Proc. Natl. Acad. Sci., USA: 81 583–587, 1984)

Non-enzymatic glycation of proteins is a crucial process in the ageing of human tissue.

This reaction, discovered by Maillard, explains the reticulation of extracellular matrices and base membranes which are mainly responsible for pathologies observed in diabetics.

In addition, Schiff's bases catalyse the production of reactive forms of oxygen, which worsen the effects of non-enzymatic glycation.

The in tubo tests are carried out on I-type collagen incubated for 21 days at 45° C. in the presence of 1% (p/v) glucose.

The rate of the Schiff's bases is assessed by fluorimetry at 430 nm (excitation at 350 nm) in the substances floating on the surface (fs) and in the centrifuging deposits (fgc). The result is given as percent inhibition relative to the control material without plant extract.

VII) Activation of Lipolysis On Human Adipocytes in "in vitro" Survival

Lipolysis is removal of triglycerides (or TG) stored in the adipocytes by an enzyme, triglyceride lipase (or TGL), causing the TG to be split into free fatty acid and glycerol, which are eliminated in the bloodstream.

The fatty acids can then be absorbed by muscle cells to produce energy.

The in vitro test is carried out as described below:

Activation of lipolysis is metered by spectrophotometric metering of the rate of glycerin salted out by adipocytes, incubated "in vitro" with the substance to be tested present.

The adipocytes are liberated by enzymatic digestion of subcutaneous human tissue by the so-called Rodbell method (Rodbell M., "Metabolism of isolated fat cells", The journal of biological chemistry, vol. 239, no. 2, pages 375 to 380, 1964).

The plant extracts are dissolved in a defined medium which is put into contact with the adipocytes for 90 minutes at 37° C.

The rate of salted-out glycerin is quantified by spectrophotometry in a medium which floats on the surface by the method of Carpéné C. and colleagues (J. Pharmacol., vol. 12, no. 2, pages 219–224, 1981).

The rate of liberated glycerin is given relative to the rate of all lipids metered by turbidimetry. The result is given as a percent increase relative to the control material without plant extract.

The comparative substances are theophylline and isoprenaline.

The results of test series V), VI) and VII) are summarised in the following table:

| Plant | Type of extract | Tyrosinase C150 | CA50 | Anti-glycation (%1) fs | fgc | B16 melanin Dose | Index | Mel. extra | Lipolysis % increase |
|---|---|---|---|---|---|---|---|---|---|
| Clidemia hirta | Aqueous E. | 0.31 | | 37 | 50 | | | | |
| Inga bourgoni | Aqueous E. | 0.060 | | 100 | 76 | 0.05 | 3.9 | 68 | |
| | Ethanol E50% | 0.070 | | | | 0.03 | 3.5 | 80 | |
| | Ethanol E. | 0.010 | | | | 0.02 | 1.4 | 10 | |
| Sabicea cinerea | Aqueous E. | | | 21 | 50 | | | | |
| | Ethanol E50% | 0.090 | | | | 0.01 | 1.6 | 49 | |
| | Ethanol E. | 0.060 | | | | 0.03 | 1.8 | 10 | |
| Astrocaryum vulgare | Aqueous E. | | | | | | | | |
| | Ethanol E50% | 0.63 | | | | | | | |
| | Ethanol E. | 0.23 | | | | | | | |
| Siparuna quianensis | Aqueous E. | | | | | | | | |
| | Methanol E80% | | | | | | | | |
| | Ethanol E. | | | | | | | | |
| Eperua falcata | Aqueous E. | | | 97 | 46 | | | | |
| | Methanol E80% | 0.38 | | | | | | | 30 |
| | Ethanol E. | 0.080 | | | | 0.01 | 1.5 | 93 | |
| Byrsonima verb. | Aqueous E. | 0.090 | | | | 0.02 | 1.7 | 72 | |
| | Methanol E80% | 0.050 | | | | 0.02 | 2.5 | 91 | |
| | Ethanol E. | 0.010 | | | | 0.03 | 2.5 | 58 | |
| Priva lappulacea | Aqueous E. | 0.35 | | | | | | | |
| | Methanol E80% | 0.13 | | | | | | | |
| | Ethanol E. | 0.060 | | | | | | | |
| Goupia glabra | Aqueous E. | | 0.037 | | | | | | |
| | Methanol E80% | | | | | | | | |
| Coutoubea spicata | Aqueous E. | 0.64 | | | | | | | |
| | Methanol E80% | 0.39 | | | | | | | |
| | Ethanol E. | 0.27 | | | | | | | |

In the above table:

C150: concentration of active substances by weight/volume giving 50% inhibition

CA50: concentration of active substances by weight/volume giving 50% activation

Dose: concentration of active substances tested by weight/volume

Index (B16 melanin): protein rate/rate of intracellular melanin

Mel. extra: rate of extracellular melanin (salted out in the substance floating on the surface) as percent inhibition.

In evaluating the results of the above test tables the inventors worked out various preferred embodiments of the invention.

To obtain a cosmetic or dermo-pharmaceutical composition giving an increased anti-elastase action as well as an anti-radical-type action, the active ingredient contained in said composition and passing on these properties is advantageously formed by at least one extract of a plant selected from the group formed by *Clidemia hirta, Inga bourgoni, Sabicea cinerea, Astrocaryum vulgare, Siparuna guianensis, Eperua falcata, Byrsonima verbascifolia* and *Priva lappulacea*.

To obtain a cosmetic or dermo-pharmaceutical composition giving an increased anti-collagenase action as well as an anti-radical-type action, the active ingredient contained in said composition and passing on these properties is advantageously formed by at least one extract of a plant selected from the group formed by *Clidemia hirta, Inga bourgoni, Sabicea cinerea, Astrocaryum vulgare, Siparuna guianensis, Eperua falcata, Byrsonima verbascifolia* and *Priva lappulacea*.

To obtain a cosmetic or dermo-pharmaceutical composition giving an increased de-pigmenting action as well as an anti-radical-type action, the active ingredient contained in said composition and passing on these properties is advantageously formed by at least one extract of a plant selected from the group formed by *Clidemia hirta, Inga bourgoni, Sabicea cinerea, Eperua falcata, Byrsonima verbascifolia, Priva lappulacea, Astrocaryum vulgare* and *Coutoubea spicata*.

To obtain a cosmetic or dermo-pharmaceutical composition giving an important anti-UVB action as well as an anti-radical-type action, the active ingredient contained in said composition and passing on these properties is advantageously formed by at least one extract of a plant selected from the group formed by *Clidemia hirta, Inga bourgoni, Sabicea cinerea, Astrocaryum vulgare, Siparuna guianensis, Eperua falcata, Byrsonima verbascifolia* and *Priva lappulacea*.

To obtain a cosmetic or dermo-pharmaceutical composition giving an important anti-UVA action as well as an anti-radical-type action, the active ingredient contained in said composition and passing on these properties is advantageously formed by at least one extract of a plant selected from the group formed by *Clidemia hirta, Inga bourgoni, Sabicea cinerea, Astrocaryum vulgare, Siparuna guianensis, Eperua falcata, Byrsonima verbascifolia* and *Priva lappulacea*.

To obtain a cosmetic or dermo-pharmaceutical composition giving an action protecting catalase from UVA as well as an anti-radical-type action, the active ingredient contained in said composition and passing on these properties is advantageously formed by at least one extract of a plant selected from the group formed by *Sabicea cinerea, Siparuna guianensis* and *Byrsonima verbascifolia*.

To obtain a cosmetic or dermo-pharmaceutical composition giving a strong anti-glycation action as well as an anti-radical-type action, the active ingredient contained in said composition and passing on these properties is advantageously formed by at least one extract of a plant selected from the group formed by *Clidemia hirta, Inga bourgoni, Sabicea cinerea* and *Eperua falcata*.

To obtain a cosmetic or dermo-pharmaceutical composition giving an important pigmenting action as well as an anti-radical-type action, the active ingredient contained in said composition and passing on these properties is advantageously formed by an extract of the *Goupia glabra* plant.

To obtain a cosmetic or dermo-pharmaceutical composition giving a considerable slimming (lipolytic) action as well as an anti-radical-type action, the active ingredient contained in said composition and passing on these properties is advantageously formed by an extract of the *Eperua falcata* plant.

However the active ingredient is preferably formed by an extract or a mixture of extracts obtained from one or more plants selected from the group formed by *Clidemia hirta, Inga bourgoni, Sabicea cinerea, Astrocaryum vulgare, Siparuna guianensis, Eperua falcata, Byrsonima verbascifolia* and *Priva lappulacea*.

The object of the present invention also concerns a cosmetic or dermo-pharmaceutical composition for topical, external use on the skin, mucous membrane and/or the epithelium or body appendages, characterised in that it contains a plant extract as the active ingredient giving an anti-radical-type action in particular, alone or with at least one other added ingredient, the botanical genus of the plant belonging to the group formed by the *Clidemia, Inga, Sabicea, Astrocaryum, Siparuna, Eperua, Byrsonima, Priva, Couloubea* and *Groupia* genera, and that a plant in the group formed by *Clidemia hirta, Inga bourgoni, Sabicea cinerea, Astrocaryum vulgare, Siparuna guianensis, Eperua falcata, Byrsonima verbascifolia, Priva lappulacea, Coutoubea spicata* and *Goupia glabra* is preferably selected.

According to the other additional properties relating to the anti-radical-type action which the cosmetic or dermo-pharmaceutical composition may need to provide, the group of plants which may be selected from the above-mentioned ones will contain various representatives according to the action of each of them disclosed in the tables showing the results of the tests described above.

Thus in a first embodiment of the invention the cosmetic or dermo-pharmaceutical composition may contain an active ingredient with an anti-UVA, anti-UVB and anti-collagenase action, which is formed by at least one extract of a plant selected from the group formed by *Clidemia hirta, Inga bourgoni, Sabicea cinerea, Astrocaryum vulgare, Siparuna guianensis, Eperua falcata* and *Byrsonima verbascifolia*.

In a second embodiment of the invention the cosmetic or dermo-pharmaceutical composition may contain an active ingredient with an anti-UVA, anti-UVB, anti-collagenase and anti-elastane action, which is formed by at least one extract of a plant selected from the group formed by *Clidemia hirta, Inga bourgoni, Sabicea cinerea, Astrocaryum vulgare, Siparuna guianensis, Eperua falcata* and *Byrsonima verbascifolia*.

In a third embodiment of the invention the cosmetic or dermo-pharmaceutical composition may contain an active ingredient with an anti-UVA, anti-UVB, anti-collagenase and anti-glycation action, which is formed by at least one extract of a plant selected from the group formed by *Clidemia hirta, Inga bourgoni, Sabicea cinerea* and *Eperua falcata*.

In a fourth embodiment of the invention the cosmetic or dermo-pharmaceutical composition may contain an active ingredient with an anti-UVA, anti-UVB, anti-collagenase, anti-elastane and de-pigmenting action, which is formed by at least one extract of a plant selected from the group formed by *Clidemia hirta, Inga bourgoni, Sabicea cinerea, Eperua falcata* and *Byrsonima verbascifolia*.

In a fifth embodiment of the invention the cosmetic or dermo-pharmaceutical composition may contain an active ingredient with a pigmenting action, which is formed by an extract from the *Goupia glabra* plant.

In a sixth embodiment of the invention the cosmetic or dermo-pharmaceutical composition may contain an active ingredient with a slimming action, which is formed by an extract from the *Eperua falcata* plant.

The cosmetic composition advantageously contains as its active ingredient—alone or combined with other active ingredients—between 0.001% and 20% by weight, preferably between 0.1% and 3% by weight, of an extract or mixture of extracts from a plant or plants defined and obtained in the above-mentioned manner.

The extract or mixture of extracts forming an active ingredient may be used in any galenic form possible in cosmetics, particularly in a galenic form chosen from oil in water emulsions, water in oil emulsions, face lotions, cosmetic milk, gels, hydrogels, cremes, pomades, soaps, pellets, spraying materials, hair lotion and shampoos.

The extract or mixture of extracts may also be added to one or more cosmetic vectors, particularly one or more vectors selected from the group formed by liposomes, macrocapsules, microcapsules, nanocapsules, macroparticles, microparticles and nanoparticles.

Various products or cosmetic preparations containing a plant extract as described above will now be described, as examples to which the practical use of the invention is not limited.

EXAMPLE 1

A cosmetic product in the form of a skin bleaching cream may for example be of the following composition by weight:

| Fraction A: | |
|---|---|
| Glycerin stearate and Ceteareth-20 | 15.0% |
| Paraffin oil | 3.0% |
| Ascorbyl palmitate | 3.0% |
| Dimethicon | 3.0% |
| Cetyl alcohol | 0.5% |
| PEG 30 glycerol isostearate | 2.0% |
| Fraction B: | |
| Water | 72.2% |
| Methyl parabene | 0.2% |
| Imidazolinidyl urea | 0.3% |
| Ethanol extract of *Inga bourgoni* | 0.5% |
| Fraction C | |
| Perfume | 0.3% |

The procedure for preparing this cream consists of melting the Fraction A constituents with agitation at 75° C., preparing Fraction B at 75° C. then pouring Fraction B into Fraction A with turbine agitation, cooling with planetary agitation then adding to Fraction C.

EXAMPLE 2

A cosmetic product in the form of an anti-blotch emulsion for the hands, to treat cutaneous pigment marks, may for example be of the following composition by weight.

In accordance with the invention the product could alternatively have multiple actions, particularly anti-radical, anti-elastase and anti-collagenase.

| Fraction A: | |
|---|---|
| Glycerin stearate and PEG 100 stearate | 6.0% |
| Olein alcohol | 1.5% |
| Glycerin stearate | 2.0% |
| Steareth 2 | 2.0% |
| Karité butter | 3.0% |
| Dimethicon | 4.0% |
| Caprylic capric triglyceride | 8.0% |
| Propyl parabene | 0.1% |
| Tocopherol acetate | 0.1% |
| Fraction B: | |
| Water | 60.8% |
| Elastab 388 (Laboratoires Sérobiologiques) | 2.5% |
| *Byrsonima verbascifolia* extract (80% methanol) | 1.5% |
| Ethanol *Astrocaryum vulgare* extract | 1.5% |
| Propylene glycol | 5.0% |
| Fraction C: | |
| Polyacrylamide, isoparaffin and Laureth 7 | 2.0% |

The procedure for making this emulsion consists of preparing Fractions A and B separately at 75° C., adding Fraction A to Fraction B with turbine agitation at 75° C., cooling to 50° C. then adding Fraction C and lastly cooling the final mixture to ambient temperature.

EXAMPLE 3

A cosmetic product in the form of an anti-wrinkle day cream and a multiple-action anti-ageing cream may for example be of the following composition by weight:

| Fraction A: | |
|---|---|
| Glycerin stearate | 14.0% |
| Octyl dodecanol | 16.0% |
| Dibutyl adipate | 6.0% |
| Ceteareth 12 | 1.5% |
| Ceteareth 20 | 1.5% |
| Fraction B: | |
| Propylene glycol | 5.0 |
| Aqueous extract of *Inga bourgoni* | 3.25% |
| Extract of *Sabicea cinerea* (50% ethanol) | 1.0% |
| Ethanol extract of *Eperua falcata* | 0.75% |
| Elastab 4112 (Laboratoires Sérobiologiques) | 0.4% |
| Water | 50.6% |
| Fraction C: | |
| Perfume | 0.3% |

The procedure for making the cream comprises preparing Fractions A and B separately at 80° C. with agitation, adding Fraction A to Fraction B with turbine agitation, cooling the mixture to 45° C. then adding Fraction C, and lastly bringing the final mixture back to ambient temperature.

The invention is not of course restricted to the embodiments described and illustrated in the accompanying drawings. Modifications are possible, particularly in the composition of the various elements or through replacement by industrial equivalents, without thereby going beyond the scope of the invention.

What is claimed is:

1. A composition for topical application to skin, mucous membrane, epithelium, body appendages or combinations thereof, characterized in that said composition contains a first active ingredient, alone or combined with a second active ingredient, wherein said first active ingredient is an extract of *Inga bourgoni*.

2. A composition according to claim 1, characterized in that it contains a second active ingredient with a pigmenting action, formed by an extract from a *Goupia glabra* plant.

3. A composition according to claim 1, characterized in that said composition contains a second active ingredient with a slimming action, formed by an extract from an *Eperua falcate* plant.

4. A composition according to claim 1, characterized in that said composition contains said first active ingredient in an amount between 0.001% and 20% by weight of an extract or a mixture of extracts.

5. A composition according to claim 1, characterized in that the extract or mixture of extracts form an active ingredient which is used in a galenic form selected from the group consisting of oil in water emulsions, water in oil emulsions, face lotions, cosmetic milk, gels, hydrogels, cremes, pomades, soaps, pellets, spraying materials, hair lotion and shampoos.

6. A composition according to claim 1, characterized in that the extract or mixture of extracts is added to one or more cosmetic vectors selected from the group consisting of liposomes, macrocapsules, microcapsules, nanocapsules, macroparticles, microparticles and nano-particles.

* * * * *